United States Patent
Tratrat et al.

(10) Patent No.: US 11,820,779 B1
(45) Date of Patent: Nov. 21, 2023

(54) AZA-PODOPHYLLOTOXIN ANALOGUES AS POTENTIAL ANTI-CANCER AGENTS

(71) Applicant: KING FAISAL UNIVERSITY, Al-Ahsa (SA)

(72) Inventors: Christophe Tratrat, Al-Ahsa (SA); Michelyne Haroun, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/122,047

(22) Filed: Mar. 15, 2023

(51) Int. Cl.
| | |
|---|---|
| *C07D 491/147* | (2006.01) |
| *C07D 495/14* | (2006.01) |
| *C07D 487/04* | (2006.01) |
| *A61P 35/00* | (2006.01) |
| *C07D 487/14* | (2006.01) |

(52) U.S. Cl.
CPC .......... *C07D 491/147* (2013.01); *A61P 35/00* (2018.01); *C07D 487/14* (2013.01); *C07D 495/14* (2013.01)

(58) Field of Classification Search
CPC . C07D 491/147; C07D 487/14; C07D 495/14
See application file for complete search history.

(56) References Cited

U.S. PATENT DOCUMENTS

| | | |
|---|---|---|
| 2013/0245048 A1 | 9/2013 | Ahmed et al. |
| 2014/0187500 A1 | 7/2014 | Movassagh et al. |
| 2019/0077808 A1 | 3/2019 | Pettit et al. |
| 2019/0255187 A1 | 8/2019 | Movassagh et al. |
| 2021/0128705 A1 | 5/2021 | Kumar |

OTHER PUBLICATIONS

Registry No. 669718-25-6, File Registry on STN, Apr. 1, 2004.*
N,6,7-Trimethyl-4-amino-1,4a,9-triaza-4aH-fluorene-2,3-dicarbimide, PubChem, 2006.
N-Methyl-4-amino-1,4a,9-triaza-4aH-fluorene-2,3-dicarbimide, PubChem, 2007.
12,12-Dimethyl-13-oxa-1,8,10-triazatetracyclo[7.7.0.02,7.011,15]hexadeca-2,4,6,8,11(15)-pentaene-14,16-dione, PubChem, 2019.
12,12-diethyl-13-oxa-1,8,10-triazatetracyclo[7.7.0.02,7.011,15]hexadeca-2,4,6,8,11(15)-pentaene-14,16-dione, PubChem, 2019.
Shah et al., "Podophyllotoxin: History, Recent Advances and Future Prospects," Biomolecules. Apr. 2021; 11(4): 603.
Pettit et al., "Antineoplastic Agents. 585. Isolation of Bridelia ferruginea Anticancer Podophyllotoxins and Synthesis of 4-Aza-podophyllotoxin Structural Modifications," J. Nat. Prod. 2016, 79, 3, 507-518.
Shi et al., "Facile synthesis of new 4-aza-podophyllotoxin analogs via microwave-assisted multi-component reactions and evaluation of their cytotoxic activity," Bioorganic & Medicinal Chemistry Letters, vol. 21, Issue 23, Dec. 1, 2011, pp. 7119-7123.

* cited by examiner

Primary Examiner — Rebecca L Anderson
(74) Attorney, Agent, or Firm — Nath, Goldberg & Meyer; Richard C. Litman

(57) ABSTRACT

Novel tetracyclic aza-podophyllotoxin analogue compounds, a method of synthesizing these compounds, a pharmaceutical composition comprising these compounds and a suitable carrier, and a method of using the compounds. The tetracyclic aza-podophyllotoxin analogue compounds are useful as antitumor agents.

11 Claims, No Drawings

AZA-PODOPHYLLOTOXIN ANALOGUES AS POTENTIAL ANTI-CANCER AGENTS

BACKGROUND

1. Field

The disclosure of the present patent application relates generally to the clinical application of novel tetracyclic aza-Podophyllotoxin analogues, for example, benzo[4,5] imidazo[1,2-a]furo[3,4-d]pyrimidin-1-ones, as potential antitumoral/anti-cancer agents.

2. Description of the Related Art

Lignans, a class of natural products found in a variety of plants, are known to play a crucial role in medicinal chemistry due to their extensive biological activity and their broad therapeutic applications. The natural aryltetralin lactone podophyllotoxin, a potent inhibitor of microtubule assembly, occupies a unique position among lignans and exhibits both antitumor and antiviral activities. Due to severe toxicity of podophyllotoxin, two synthetic analogues, Etoposide and Tenoposide, are currently in use in cancer chemotherapy. Podophyllotoxins belong to a class of natural products from which the clinically used Etoposide and Tenoposide are already known.

Numerous investigations concerning structural modifications of podophyllotoxin have been accomplished. In this context a large number of azapodophyllotoxins derivatives have been synthesized and investigated for their antitumour activity (Hua-yang Fan, Zhuo-li Zhu, Hong-chun Xian, Hao-fan Wang, Bing-jun Chen, Ya-Jie Tang, Ya-ling Tang, Xin-hua Liang, Front Cell Dev Biol., 2021; 9: 709075). Tratrat et al. made an important contribution to this field by discovering a greatly simplified one pot synthesis of azapodophylloxine analogues possessing potent cytotoxicity (Tratrat et al., Org. Lett., 2002, 4, 3187-3189). In this context a large number of 4-Aza-2,3-didehydro podophyllotoxins derivatives have been synthesized and investigated for their antitumour activity and retain most of the cytotoxicity associated with the parent lignan (M. G. Botesl, S. C. Pelly1, M. A. L. Blackiel, A. Kornienko2, and W. A. L. van Otterlo, Chemistry of Heterocyclic Compounds, 2014, 50 (2), 119-138; US 2003/006548515, US 2013/0245048, US 2019/0077808 US 2021/0128705). However, none of these analogues have been found to solve all previously known problems with this class of compounds.

It would be desirable to have clinical applications of synthetic analogues in addition to or instead of the Etoposide and Tenoposide that are currently in use in cancer chemotherapy, such as derivatives that demonstrate good to excellent cytotoxic activity against a large panel of cancer cell lines at a nano-molar concentration range with structures that are easily amended to target different drug actions such as topoisomerases, tubulin, and kinases as important molecular targets of currently clinically used anticancer agents.

Thus, new podophyllotoxin compound solving the aforementioned problems are desired.

SUMMARY

The present subject matter relates to new antitumor agents with potentially new mechanisms of action alongside those already existing for a certain class of antitumor agents. Accordingly, the present subject matter relates to new aza-podophyllotoxins as potential anticancer agents.

The present subject matter provides novel tetracyclic aza-podophyllotoxin analogue compounds, for example, benzo[4,5]imidazo[1,2-a]furo[3,4-d]pyrimidin-1-one compounds of the general formula/structure I, as useful antitumor agents. The present subject matter further provides a process for the synthesis of aza-podophyllotoxin analogue compounds and their use in therapy for the treatment of cancer as a sole active agent or in combination with other active ingredients.

In one embodiment, the present subject matter relates to compounds of formula I:

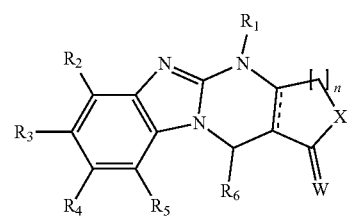

or a pharmaceutically acceptable salt, ester stereoisomer, or solvate thereof, wherein:

⇝ represents a single or double bond;

n is 1 or 2;

W represents an oxygen or sulfur;

X represents an oxygen, sulfur, $CH_2$, or $-NR_7$ wherein $R_7$ represents a hydrogen atom or a linear or branched $(C_1-C_6)$alkyl group, a $(C_3-C_9)$cycloalkyl group, a $(C_1-C_6)$ alkyl-aryl group, an aryl group, or a heteroaryl group;

$R_1$ represents:

a hydrogen atom, aryl, heteroaryl, $(C_3-C_9)$ cycloalkyl group, linear or branched $(C_1-C_6)$ alkyl group, optionally substituted by an aryl group, a heteroaryl group, a hydroxy group, a linear or branched $(C_1-C_6)$ alkoxy group, a carboxylic acid group, a group of formula $-CONR_8R_9$ or $-NR_8R_9$, wherein $R_8$ and $R_9$, which may be the same or different, each independently represent a linear or branched $(C_1-C_6)$alkyl group optionally substituted by a hydroxy group or an amino group (itself optionally substituted by one or two linear or branched $(C_1-C_6)$ alkyl groups), or $R_8$ and $R_9$, together with the nitrogen atom to which they are attached, form a nitrogen-containing heterocycle, an amino group optionally substituted by one or more aryl groups, heteroaryl groups, or linear or branched $(C_1-C_6)$ alkyl groups or $(C_3-C_6)$ cycloalkyl groups optionally substituted by a carboxylic acid group, or by a group of formula $-CONR_8R_9$ or $-NR_8R_9$, or $-OR_{10}$ wherein $R_{10}$ represents a hydrogen atom, an aryl group, a heteroaryl group, or a linear or branched $(C_1-C_6)$ alkyl group or a $(C_3-C_6)$ cycloalkyl group optionally substituted by a carboxylic acid group, or by a group of formula $-CONR_8R_9$ or $-NR_8R_9$;

$R_2$, $R_3$, $R_4$, and $R_5$, which may be the same or different, each represent:
a hydrogen atom,
a halogen atom,
a hydroxy group,
a nitro group,
a linear or branched ($C_1$-$C_6$) polyhaloalkyl group,
a linear or branched ($C_1$-$C_6$) alkyl group,
—$OR_{10}$,
an amino group,
a substituted amino group optionally substituted by one or more aryl groups, heteroaryl groups, or linear or branched ($C_1$-$C_6$) alkyl groups or ($C_3$-$C_6$) cycloalkyl groups optionally substituted by a carboxylic acid group, by a carbonyl group, or by a group of formula —$CONR_8R_9$ or —$NR_8R_9$,
—$OPO(OH)_2$,
an acyl group,
a carboxylic acid group,
a sulfonyl group,
a sulfonamide group, or
a cyano group; and
$R_6$ is a hydrogen atom, a linear or branched ($C_1$-$C_6$) alkyl group, a ($C_3$-$C_6$) cycloalkyl group, or an aryl or heteroaryl group optionally substituted in one or more positions with one or more of $R_2$, $R_3$, $R_4$, and $R_5$, each of which may be the same or different.

In a further embodiment, the present subject matter relates to an aza-Podophyllotoxin analogue compound of formula I:

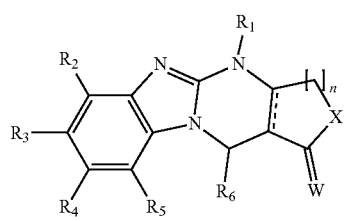

I or a pharmaceutically acceptable salt, ester stereoisomer, or solvate thereof, wherein:
n is 1;
W is O;
X is O, NH or S;
$R_1$ is H;
$R_2$, $R_3$, $R_4$ and $R_5$ are each H; and
$R_6$ is phenyl or benzo[d][1,3]dioxolyl, each of which may be optionally substituted with one or more substituents independently selected from the group consisting of hydroxy, methoxy, methyl, $N(CH_3)_2$, $NH_2$, —$NHCOCH_3$, fluorine, bromine, and chlorine.

In an embodiment, the present subject matter relates to a compound selected from the group consisting of:
11-(4-methoxyphenyl)-4,11-dihydro-1H,3H-benzo[4,5]imidazo[1,2-a]furo[3,4-d]pyrimidin-1-one (1),
11-(3,4-dimethoxyphenyl)-4,11-dihydro-1H,3H-benzo[4,5]imidazo[1,2-a]furo[3,4-d]pyrimidin-1-one (2),
11-(3,4,5-trimethoxyphenyl)-4,11-dihydro-1H,3H-benzo[4,5]imidazo[1,2-a]furo[3,4-d]pyrimidin-1-one (3),
11-(benzo[d][1,3]dioxol-5-yl)-4,11-dihydro-1H,3H-benzo[4,5]imidazo[1,2-a]furo[3,4-d]pyrimidin-1-one (4),
11-(3,4-dihydroxyphenyl)-4,11-dihydro-1H,3H-benzo[4,5]imidazo[1,2-a]furo[3,4-d]pyrimidin-1-one (5),
11-(4-hydroxy-3-methoxyphenyl)-4,11-dihydro-1H,3H benzo[4,5]imidazo[1,2-a]furo[3,4-d]pyrimidin-1-one (6),
11-(p-tolyl)-4,11-dihydro-1H,3H-benzo[4,5]imidazo[1,2-a]furo[3,4-d]pyrimidin-1-one (7),
11-(4-(dimethylamino)phenyl)-4,11-dihydro-1H,3H-benzo[4,5]imidazo[1,2-a]furo[3,4-d]pyrimidin-1-one (8),
11-(4-aminophenyl)-4,11-dihydro-1H,3H-benzo[4,5]imidazo[1,2-a]furo[3,4-d]pyrimidin-1-one (9),
N-(4-(1-oxo-4,11-dihydro-1H,3H-benzo[4,5]imidazo[1,2-a]furo[3,4-d]pyrimidin-11-yl)phenyl)acetamide (10),
11-(3,4,5-trimethoxyphenyl)-2,3,4,11-tetrahydro-1H-benzo[4,5]imidazo[1,2-a]pyrrolo[3,4-d]pyrimidin-1-one (11),
11-(3,4,5-trimethoxyphenyl)-4,11-dihydro-1H,3H-benzo[4,5]imidazo[1,2-a]thieno[3,4-d]pyrimidin-1-one (12),
11-(4-fluorophenyl)-4,11-dihydro-1H,3H-benzo[4,5]imidazo[1,2-a]furo[3,4-d]pyrimidin-1-one (13),
11-(4-chlorophenyl)-4,11-dihydro-1H,3H-benzo[4,5]imidazo[1,2-a]furo[3,4-d]pyrimidin-1-one (14),
1-(4-bromophenyl)-4,11-dihydro-1H,3H-benzo[4,5]imidazo[1,2-a]furo[3,4-d]pyrimidin-1-one (15),
and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of treating various cancers by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., C1-C40 alkyl group), for example, 1-30 carbon atoms (i.e., C1-C30 alkyl group). In some embodiments, an alkyl group can have 1 to 6 carbon atoms, and can be referred to as a "lower alkyl group" or a "C1-C6 alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-C40 alkenyl group), for example, 2 to 20 carbon atoms (i.e., C2-C20 alkenyl group) or 2 to 6 carbon atoms (i.e., C2-C6 alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-C24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH2, SiH(alkyl), Si(alkyl)2, SiH(arylalkyl), Si(arylalkyl)2, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the instant application the terms "benzo[4,5]imidazo[1,2-a]furo[3,4-d]pyrimidin-1-one derivatives", "tetracyclic aza-Podophyllotoxin analogues of benzo[4,5]imidazo[1,2-a]furo[3,4-d]pyrimidin-1-one", "aza-Podophyllotoxin analogue compounds", "benzimidazofuropyrimidin-1-one derivatives", and the like may be used interchangeably.

Aza-Podophyllotoxin Analogue Compounds

In one embodiment, the present subject matter may include aza-Podophyllotoxin analogue compounds having the Structure I:

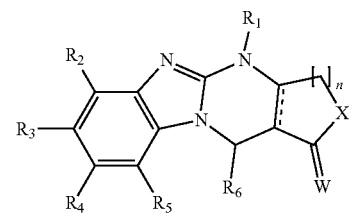

I or a pharmaceutically acceptable salt, ester stereoisomer, or solvate thereof, wherein:

⟍ represents a single or double bond;

n is 1 or 2;

W represents an oxygen or sulfur;

X represents an oxygen, sulfur, $CH_2$, or $-NR_7$ wherein $R_7$ represents a hydrogen atom or a linear or branched ($C_1$-$C_6$)alkyl group, a ($C_3$-$C_9$)cycloalkyl group, a ($C_1$-$C_6$) alkyl-aryl group, an aryl group, or a heteroaryl group;

$R_1$ represents:

a hydrogen atom, aryl, heteroaryl, ($C_3$-$C_9$) cycloalkyl group, linear or branched ($C_1$-$C_6$) alkyl group, optionally substituted by an aryl group, a heteroaryl group, a hydroxy group, a linear or branched ($C_1$-$C_6$) alkoxy group, a carboxylic acid group, a group of formula $-CONR_8R_9$ or $-NR_8R_9$, wherein $R_8$ and $R_9$, which may be the same or different, each independently represent a linear or branched ($C_1$-$C_6$)alkyl group optionally substituted by a hydroxy group or an amino group (itself optionally substituted by one or two linear or branched ($C_1$-$C_6$) alkyl groups), or $R_8$ and $R_9$, together with the nitrogen atom to which they are attached, form a nitrogen-containing heterocycle, an amino group optionally substituted by one or more aryl groups, heteroaryl groups, or linear or branched ($C_1$-$C_6$) alkyl groups or ($C_3$-$C_6$) cycloalkyl groups optionally substituted by a carboxylic acid group, or by a group of formula —$CONR_8R_9$ or —$NR_8R_9$, or —$OR_{10}$ wherein $R_{10}$ represents a hydrogen atom, an aryl group, a heteroaryl group, or a linear or branched ($C_1$-$C_6$) alkyl group or a ($C_3$-$C_6$) cycloalkyl group optionally substituted by a carboxylic acid group, or by a group of formula —$CONR_8R_9$ or —$NR_8R_9$;

$R_2$, $R_3$, $R_4$, and $R_5$, which may be the same or different, each represent:
a hydrogen atom,
a halogen atom,
a hydroxy group,
a nitro group,
a linear or branched ($C_1$-$C_6$) polyhaloalkyl group,
a linear or branched ($C_1$-$C_6$) alkyl group,
—$OR_{10}$,
an amino group,
a substituted amino group optionally substituted by one or more aryl groups, heteroaryl groups, or linear or branched ($C_1$-$C_6$) alkyl groups or ($C_3$-$C_6$) cycloalkyl groups optionally substituted by a carboxylic acid group, by a carbonyl group, or by a group of formula —$CONR_8R_9$ or —$NR_8R_9$,
—$OPO(OH)_2$,
an acyl group,
a carboxylic acid group,
a sulfonyl group,
a sulfonamide group, or
a cyano group; and $R_6$ is a hydrogen atom, a linear or branched ($C_1$-$C_6$) alkyl group, a ($C_3$-$C_6$) cycloalkyl group, or an aryl or heteroaryl group optionally substituted in one or more positions with one or more of $R_2$, $R_3$, $R_4$, and $R_5$, each of which may be the same or different.

In a further embodiment, the present subject matter relates to an aza-Podophyllotoxin analogue compound of formula I, wherein n is 1.

In another embodiment, the present subject matter relates to compounds of formula I, wherein W is O.

In yet another embodiment, the present subject matter relates to compounds of formula I, wherein X is S, NH, or O.

In still yet another embodiment, the present subject matter relates to compounds of formula I, wherein $R_1$ is H.

In a further embodiment, the present subject matter relates to compounds of formula I, wherein $R_2$, $R_3$, $R_4$, and $R_5$ are each H.

In another embodiment, the present subject matter relates to a compound of formula I, wherein $R_6$ is phenyl or benzo[d][1,3]dioxolyl, each of which may be optionally substituted with one or more substituents independently selected from the group consisting of hydroxy, methoxy, methyl, $N(CH_3)_2$, $NH_2$, —$NHCOCH_3$, fluorine, bromine, and chlorine. In one embodiment in this regard, $R_6$ is phenyl substituted by 1, 2, or 3 methoxy groups. In another embodiment in this regard, $R_6$ is phenyl substituted by 1 or 2 hydroxy groups, or by one hydroxy group and one methyl group.

In an embodiment, the present subject matter relates to a compound selected from the group consisting of:
11-(4-methoxyphenyl)-4,11-dihydro-1H,3H-benzo[4,5]imidazo[1,2-a]furo[3,4-d]pyrimidin-1-one (1),
11-(3,4-dimethoxyphenyl)-4,11-dihydro-1H,3H-benzo[4,5]imidazo[1,2-a]furo[3,4-d]pyrimidin-1-one (2),
11-(3,4,5-trimethoxyphenyl)-4,11-dihydro-1H,3H-benzo[4,5]imidazo[1,2-a]furo[3,4-d]pyrimidin-1-one (3),
11-(benzo[d][1,3]dioxol-5-yl)-4,11-dihydro-1H,3H-benzo[4,5]imidazo[1,2-a]furo[3,4-d]pyrimidin-1-one (4),
11-(3,4-dihydroxyphenyl)-4,11-dihydro-1H,3H-benzo[4,5]imidazo[1,2-a]furo[3,4-d]pyrimidin-1-one (5),
11-(4-hydroxy-3-methoxyphenyl)-4,11-dihydro-1H,3H benzo[4,5]imidazo[1,2-a]furo[3,4-d]pyrimidin-1-one (6),
11-(p-tolyl)-4,11-dihydro-1H,3H-benzo[4,5]imidazo[1,2-a]furo[3,4-d]pyrimidin-1-one (7),
11-(4-(dimethylamino)phenyl)-4,11-dihydro-1H,3H-benzo[4,5]imidazo[1,2-a]furo[3,4-d]pyrimidin-1-one (8),
11-(4-aminophenyl)-4,11-dihydro-1H,3H-benzo[4,5]imidazo[1,2-a]furo[3,4-d]pyrimidin-1-one (9),
N-(4-(1-oxo-4,11-dihydro-1H,3H-benzo[4,5]imidazo[1,2-a]furo[3,4-d]pyrimidin-11-yl)phenyl)acetamide (10),
11-(3,4,5-trimethoxyphenyl)-2,3,4,11-tetrahydro-1H-benzo[4,5]imidazo[1,2-a]pyrrolo[3,4-d]pyrimidin-1-one (11),
11-(3,4,5-trimethoxyphenyl)-4,11-dihydro-1H,3H-benzo[4,5]imidazo[1,2-a]thieno[3,4-d]pyrimidin-1-one (12),
11-(4-fluorophenyl)-4,11-dihydro-1H,3H-benzo[4,5]imidazo[1,2-a]furo[3,4-d]pyrimidin-1-one (13),
11-(4-chlorophenyl)-4,11-dihydro-1H,3H-benzo[4,5]imidazo[1,2-a]furo[3,4-d]pyrimidin-1-one (14),
11-(4-bromophenyl)-4,11-dihydro-1H,3H-benzo[4,5]imidazo[1,2-a]furo[3,4-d]pyrimidin-1-one (15),
and a pharmaceutically acceptable salt, ester stereoisomer, or solvate thereof.

In the present subject matter, the structures of the above compounds are illustrated as follows:

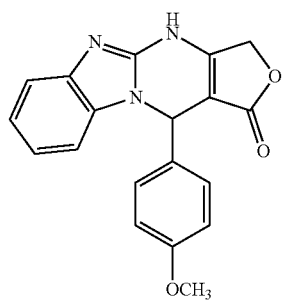

1

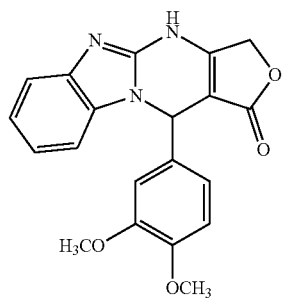

2

-continued
3
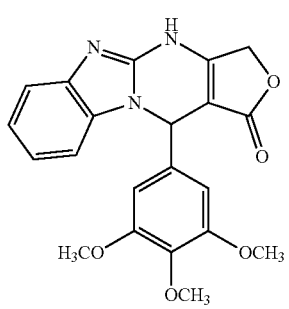
4
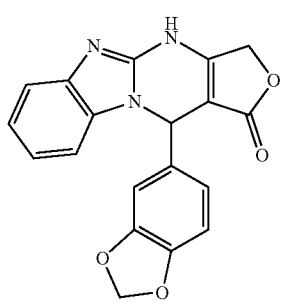
5
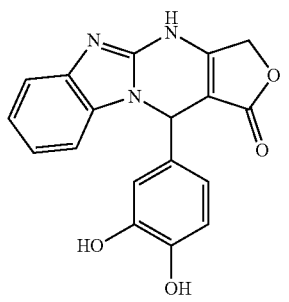
6
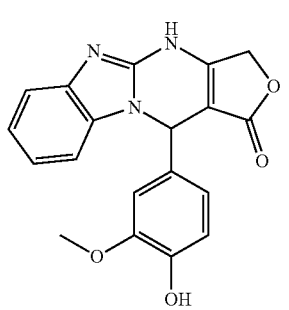
7
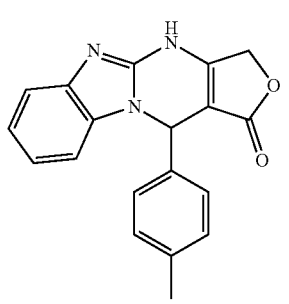
-continued
8
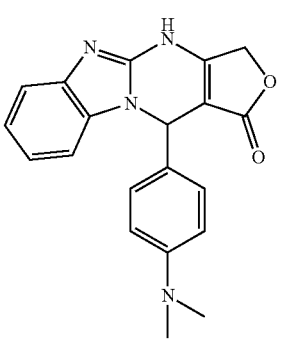
9
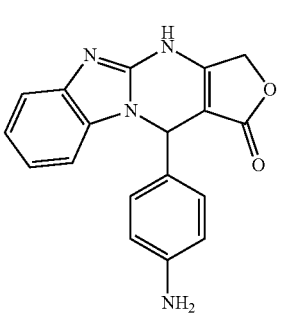
10
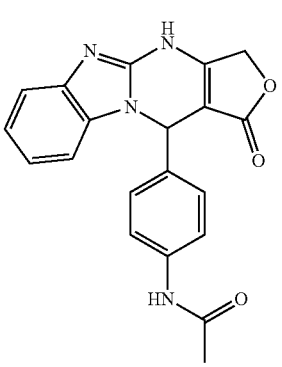
11
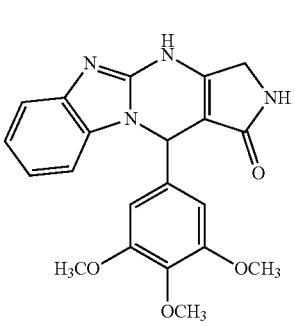
12
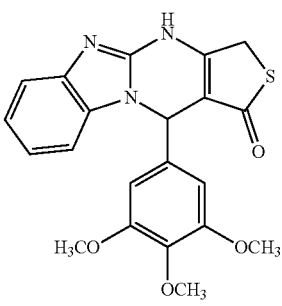

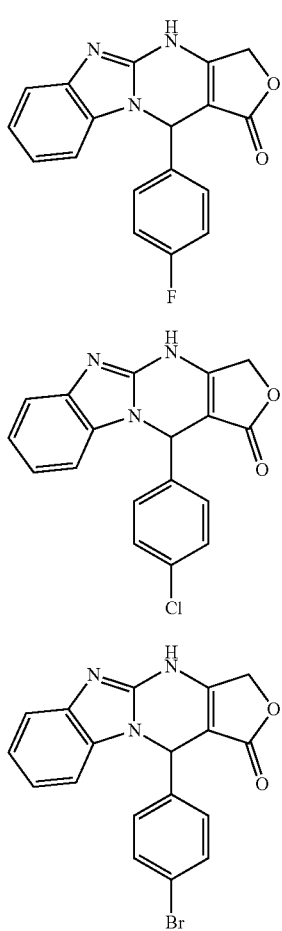

and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or the salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, sub salicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

Synthesis:

In one embodiment, the present subject matter further relates to a process for synthesizing the aza-podophyllotoxin analogue compounds of formula/structure I, the process comprising the following general reaction scheme:

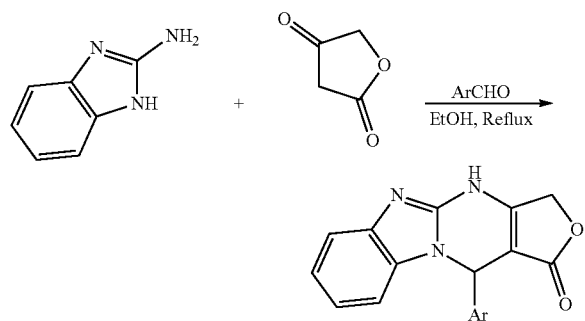

The synthesis of the derivatives of the current subject matter of structure I relies on a one pot multiple component reaction by using diverse aldehydes, 2-aminobenzimidazole and activated methylene derivative such as tetronic acid.

Pharmaceutical Compositions:

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for an acute or chronic airway disease or disorder. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of a bacterial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microtine powder for insufflation, alone or in combination with an inert carrier such as lactose. In such a case, the particles of the formulation have diameters of less than 50 microns, for example less than 10 microns.

Methods of Use:

The present compounds have valuable pharmaceutical properties, which make them commercially utilizable. Accordingly, the present subject matter further relates to use of the present compounds for the treatment of diseases such as cancers.

In another embodiment of the present subject matter, the aforementioned compound derivatives demonstrated in vitro anticancer action against human cancer cell lines comprising MCF-7 (breast cancer), A-549 (lung cancer), and HL-60 (leukemia). Accordingly, the present subject matter relates to methods of treating a cancer in a patient by administering one or more of the compounds presented herein to a patient in need thereof. In certain embodiments, the cancer is breast cancer, lung cancer, or leukemia.

In another embodiment of the present subject matter, the concentration of the present compounds engaged for in vitro study against lung cancer cell lines for IC50 was in the range of about 0.058 to 0.211 µM at an exposure period of at least 48 hrs.

In another embodiment of the present subject matter, the concentration of the present compounds engaged for in vitro study against breast cancer cell lines for IC50 was in the range of about 0.045 to 0.374 µM at an exposure period of at least 48 hrs.

In another embodiment of the present subject matter, the concentration of the present compounds engaged for in vitro study against leukemia cell lines for IC50 was in the range of 0.061 to 0.281 µM at an exposure period of at least 48 hrs.

Pharmacological Activity

The cytotoxicity activity of the compounds of the current subject matter was assessed against three cancer cell lines such as A-549 (lung cancer), MCF-7 (breast cancer) and HL-60 (leukemia) cancer cells. The biological results, reported in Table 1, demonstrated that all the derivatives of Formula I displayed potent in vitro anti-proliferative activity with nanomolar concentration on all cancer cell lines ranging from 45 nM to 374 nM. By way of example, the compound of Example 13 showed one of the most potent cytotoxic derivatives in the series with $IC_{50}$ (concentration of cytotoxic agent which inhibits proliferation of the treated cells by 50%) of 71 nM, 45 nM and 61 nM against A-549, MCF-7 and HL-60 cancer cells respectively. In conclusion, the benzimidazofuropyrimidin-1-one derivatives of the current subject matter showing highly potent cytotoxic agents may find valuable application in treating a variety of cancers either as a sole active agent or in combination with other active ingredients.

In Vitro Cytotoxic Activity Assay

Compounds 1-15 were screened for their in vitro cytotoxic behavior utilizing a 3-(4,5-dimethyl-thiazol-2-yl)-2,5-diphenyltetrazolium bromide (MTT) assay against selected cancer human cell lines consisting of MCF-7 (human breast cancer), A-549 (lung cancer) and HL-60 (leukemia) (T. Mosmann, J. Immunol. Meth., 1983, 65, 55-63). The cells were cultured at 37° C. in RMPI1640 medium supplemented with 10% fetal bovine serum, 50 IU/mL penicillin, and 50 μg/mL streptomycin in a 5% CO2 incubator. All cells were sub-cultured 3 times/week by trypsinisation. Viable cells were seeded and allowed to adhere for 12 h before a test drug was added in 96-well plates at an initial density of 1.0×105 cells/mL. Tumour cell lines were separately exposed to various concentrations of the tested compounds followed by incubation at a temperature of 37° C. during 24 h inside a medium of fresh RMPI 1640. Cells were subsequently incubated at 37° C. using MTT at 0.5 mg/mL during 4 h. After removal of supernatant, formazan crystals were dissolved in isopropanol and the optical density was measured at 570 nm. Etopside and Cisplatin were used as a positive control. The results are summarized with Etopside and Cisplatin as standard drugs in Table 1.

TABLE 1

In vitro cytotoxic activity ($IC_{50}$, μM) of benzimidazofuropyrimidinones 1-15

| Entry | Anti-proliferative activity: $IC_{50}$ (μM) | | |
|---|---|---|---|
| | A-549 | MCF-7 | HL-60 |
| 1 | 0.092 | 0.126 | 0.082 |
| 2 | 0.120 | 0.104 | 0.096 |
| 3 | 0.081 | 0.115 | 0.128 |
| 4 | 0.104 | 0.097 | 0.084 |
| 5 | 0.151 | 0.154 | 0.178 |
| 6 | 0.095 | 0.105 | 0.133 |
| 7 | 0.067 | 0.069 | 0.072 |
| 8 | 0.092 | 0.087 | 0.129 |
| 9 | 0.123 | 0.162 | 0.143 |
| 10 | 0.211 | 0.374 | 0.281 |
| 11 | 0.086 | 0.125 | 0.104 |
| 12 | 0.075 | 0.111 | 0.085 |
| 13 | 0.071 | 0.045 | 0.061 |
| 14 | 0.058 | 0.074 | 0.069 |
| 15 | 0.105 | 0.081 | 0.092 |
| Etoposide | 11.92 | 32.81 | 0.31 |
| Cisplatin | 9.25 | 15.86 | 1.16 |

[a]Cancer cell lines: A-549 (lung cancer), MCF-7 (breast cancer) and HL-60 (leukemia).

The biological results demonstrated that the compounds of Formula I displayed potent in vitro anti-proliferative activity against cancer cell lines as compared to the control drugs.

The following examples relate to various methods of manufacturing certain specific compounds as described herein.

EXAMPLES

Example 1

11-(4-methoxyphenyl)-4,11-dihydro-1H,3H-benzo[4,5]imidazo[1,2-a]furo[3,4-d]pyrimidin-1-one (1)

To a mixture of 2-aminobenzimidazole (1 mmol), 4-methoxybenzaldehyde (1.2 mmol), tetronic acid (1.2 mmol) and 10% L-proline (10 mg) in 5 mL ethanol were heated at reflux for 1 hour. After cooling at room temperature, the precipitate obtained was filtered off, washed with ethanol and then recrystallized to yield the expected product.

Elemental Analysis: Calculated: C, 68.46; H, 4.54; N, 12.61; Found: C, 68.35; H, 4.66; N, 12.72.

Example 2

11-(3,4-dimethoxyphenyl)-4,11-dihydro-1H,3H-benzo[4,5]imidazo[1,2-a]furo[3,4-d]pyrimidin-1-one (2)

The expected product is obtained in accordance with the compound described in Example 1, starting from 2-aminobenzimidazole, 3,4-dimethoxybenzaldehyde and tetronic acid.

Elemental Analysis: Calculated C, 66.11; H, 4.72; N, 11.56. Found C, 66.04; H, 4.77; N, 11.48.

Example 3

11-(3,4,5-trimethoxyphenyl)-4,11-dihydro-1H,3H-benzo[4,5]imidazo[1,2-a]furo[3,4-d]pyrimidin-1-one (3)

The expected product is obtained in accordance with the compound described in Example 1, starting from 2-aminobenzimidazole, 3,4,5-trimethoxybenzaldehyde and tetronic acid.

Elemental Analysis: Calculated C, 64.12; H, 4.87; N, 10.68. Found C, 64.31; H, 4.78; N, 10.55.

Example 4

11-(benzo[d][1,3]dioxol-5-yl)-4,11-dihydro-1H,3H-benzo[4,5]imidazo[1,2-a]furo[3,4-d]pyrimidin-1-one (4)

The expected product is obtained in accordance with the compound described in Example 1, starting from 2-aminobenzimidazole, piperonal and tetronic acid.

Elemental Analysis: Calculated C, 65.70; H, 3.77; N, 12.10. Found C, 65.89; H, 3.75; N, 12.02.

Example 5

11-(3,4-dihydroxyphenyl)-4,11-dihydro-1H,3H-benzo[4,5]imidazo[1,2-a]furo[3,4-d]pyrimidin-1-one (5)

The expected product is obtained in accordance with the compound described in Example 1, starting from 2-aminobenzimidazole, 3,4-dihydroxybenzaldehyde and tetronic acid.

Elemental Analysis: Calculated C, 64.48; H, 3.91; N, 12.53. Found C, 64.29; H, 3.82; N, 12.61.

Example 6

11-(4-hydroxy-3-methoxyphenyl)-4,11-dihydro-1H,3H-benzo[4,5]imidazo[1,2-a]furo[3,4-d]pyrimidin-1-one (6)

The expected product is obtained in accordance with the compound described in Example 1, starting from 2-aminobenzimidazole, 4-hydroxy-3-methoxybenzaldehyde and tetronic acid.

Elemental Analysis: Calculated C, 65.32; H, 4.33; N, 12.03. Found C, 65.57; H, 4.29; N, 11.88.

Example 7

11-(p-tolyl)-4,11-dihydro-1H,3H-benzo[4,5]imidazo[1,2-a]furo[3,4-d]pyrimidin-1-one (7)

The expected product is obtained in accordance with the compound described in Example 1, starting from 2-aminobenzimidazole, p-tolualdehyde and tetronic acid. Elemental Analysis:

Calculated C, 71.91; H, 4.76; N, 13.24. Found C, 70.03; H, 4.61; N, 13.35.

Example 8

11-(4-(dimethylamino)phenyl)-4,11-dihydro-1H,3H-benzo[4,5]imidazo[1,2-a]furo[3,4-d]pyrimidin-1-one (8)

The expected product is obtained in accordance with the compound described in Example 1, starting from 2-aminobenzimidazole, 4-dimethylaminobenzaldehyde and tetronic acid.

Elemental Analysis: Calculated C, 69.35; H, 5.24; N, 16.17. Found C, 69.06; H, 5.18; N, 16.09.

Example 9

11-(4-aminophenyl)-4,11-dihydro-1H,3H-benzo[4,5]imidazo[1,2-a]furo[3,4-d]pyrimidin-1-one (9)

The expected product is obtained in accordance with the compound described in Example 1, starting from 2-aminobenzimidazole, 4-aminobenzaldehyde and tetronic acid.

Elemental Analysis: Calculated C, 67.92; H, 4.43; N, 17.60. Found C, 68.15; H, 4.37; N, 17.66.

Example 10

N-(4-(1-oxo-4,11-dihydro-1H,3H-benzo[4,5]imidazo[1,2-a]furo[3,4-d]pyrimidin-11-yl)phenyl)acetamide (10)

The expected product is obtained in accordance with the compound described in Example 1, starting from 2-aminobenzimidazole, N-(4-formylphenyl)acetamide and tetronic acid.

Elemental Analysis: Calculated C, 66.66; H, 4.48; N, 15.55. Found C, 66.48; H, 4.39; N, 15.61.

Example 11

11-(3,4,5-trimethoxyphenyl)-2,3,4,11-tetrahydro-1H-benzo[4,5]imidazo[1,2-a]pyrrolo[3,4-d]pyrimidin-1-one (11)

The expected product is obtained in accordance with the compound described in Example 1, starting from 2-aminobenzimidazole, 3,4,5-trimethoxybenzaldehyde and pyrrolidine-2,4-dione.

Elemental Analysis: Calculated C, 64.28; H, 5.14; N, 14.28. Found C, 64.19; H, 5.06; N, 14.32.

Example 12

11-(3,4,5-trimethoxyphenyl)-4,11-dihydro-1H,3H-benzo[4,5]imidazo[1,2-a]thieno[3,4-d]pyrimidin-1-one (12)

The expected product is obtained in accordance with the compound described in Example 1, starting from 2-aminobenzimidazole, 3,4,5-trimethoxybenzaldehyde and thiotetronic acid.

Elemental Analysis: Calculated C, 61.60; H, 4.68; N, 10.26. Found C, 61.48; H, 4.73; N, 10.31.

Example 13

11-(4-fluorophenyl)-4,11-dihydro-1H,3H-benzo[4,5]imidazo[1,2-a]furo[3,4-d]pyrimidin-1-one (13)

The expected product is obtained in accordance with the compound described in Example 1, starting from 2-aminobenzimidazole, 4-fluorobenzaldehyde and tetronic acid.

Elemental Analysis: Calculated C, 67.29; H, 3.76; N, 13.08. Found C, 67.44; H, 3.64; N, 13.12.

Example 14

11-(4-chlorophenyl)-4,11-dihydro-1H,3H-benzo[4,5]imidazo[1,2-a]furo[3,4-d]pyrimidin-1-one (14)

The expected product is obtained in accordance with the compound described in Example 1, starting from 2-aminobenzimidazole, 4-chlorobenzaldehyde and tetronic acid.

Elemental Analysis: Calculated C, 64.01; H, 3.58; N, 12.44. Found C, 63.87; H, 3.52; N, 12.53.

Example 15

11-(4-bromophenyl)-4,11-dihydro-1H,3H-benzo[4,5]imidazo[1,2-a]furo[3,4-d]pyrimidin-1-one (15)

The expected product is obtained in accordance with the compound described in Example 1, starting from 2-aminobenzimidazole, 4-bromobenzaldehyde and tetronic acid.

Elemental Analysis: Calculated C, 56.56; H, 3.16; N, 10.99. Found C, 56.39; H, 3.28; N, 11.14.

It is to be understood that the tetracyclic aza-Podophyllotoxin analogues, for example, benzo[4,5]imidazo[1,2-a]furo[3,4-d]pyrimidin-1-one compounds, use/application, method of making, and properties of said compounds are not limited to the specific embodiments or examples described above, but encompasses any and all embodiments within the scope of the generic language of the following claims enabled by the embodiments described herein, or otherwise shown in the drawings or described above in terms sufficient to enable one of ordinary skill in the art to make and use the instant subject matter compounds.

We claim:
1. A compound having the formula I:

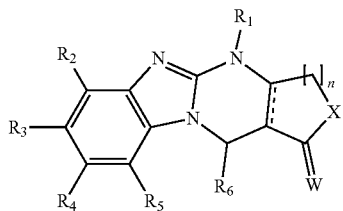

or a pharmaceutically acceptable salt, ester, stereoisomer, or solvate thereof, wherein $\diagdown$ represents a single or double bond, n is 1;

W represents oxygen (O) or sulfur (S);

X represents an oxygen, sulfur, $CH_2$, or $-NR_7$ wherein $R_7$ represents a hydrogen atom or a linear or branched $(C_1-C_6)$alkyl group, a $(C_3-C_9)$cycloalkyl group, a $(C_1-C_6)$alkyl-aryl group, an aryl group, or a heteroaryl group;

$R_1$ represents:
- a hydrogen atom,
- aryl,
- heteroaryl,
- $(C_3-C_9)$ cycloalkyl group,
- linear or branched $(C_1-C_6)$ alkyl group, optionally substituted by an aryl group, a heteroaryl group, a hydroxy group, a linear or branched $(C_1-C_6)$ alkoxy group, a carboxylic acid group, a group of formula $-CONR_8R_9$ or $-NR_8R_9$, wherein $R_8$ and $R_9$, which may be the same or different, each independently represent a linear or branched $(C_1-C_6)$alkyl group optionally substituted by a hydroxy group or an amino group (itself optionally substituted by one or two linear or branched $(C_1-C_6)$ alkyl groups), or $R_8$ and $R_9$, together with the nitrogen atom to which they are attached, form a nitrogen-containing heterocycle,
- an amino group optionally substituted by one or more aryl groups, heteroaryl groups, or linear or branched $(C_1-C_6)$ alkyl groups or $(C_3-C_6)$ cycloalkyl groups optionally substituted by a carboxylic acid group, or by a group of formula $-CONR_8R_9$ or $-NR_8R_9$, or
- $-OR_{10}$ wherein $R_{10}$ represents a hydrogen atom, an aryl group, a heteroaryl group, or a linear or branched $(C_1-C_6)$ alkyl group or a $(C_3-C_6)$ cycloalkyl group optionally substituted by a carboxylic acid group, or by a group of formula $-CONR_8R_9$ or $-NR_8R_9$;

$R_2$, $R_3$, $R_4$, and $R_5$, which may be the same or different, each represent:
- a hydrogen atom,
- a halogen atom,
- a hydroxy group,
- a nitro group,
- a linear or branched $(C_1-C_6)$ polyhaloalkyl group,
- a linear or branched $(C_1-C_6)$ alkyl group,
- $-OR_{10}$,
- an amino group,
- a substituted amino group optionally substituted by one or more aryl groups, heteroaryl groups, or linear or branched $(C_1-C_6)$ alkyl groups or $(C_3-C_6)$ cycloalkyl groups optionally substituted by a carboxylic acid group, by a carbonyl group, or by a group of formula $-CONR_8R_9$ or $-NR_8R_9$,
- $-OPO(OH)_2$,
- an acyl group,
- a carboxylic acid group,
- a sulfonyl group,
- a sulfonamide group, or
- a cyano group; and $R_6$ is a hydrogen atom, a linear or branched $(C_1-C_6)$ alkyl group, a $(C_3-C_6)$ cycloalkyl group, or an aryl or heteroaryl group optionally substituted in one or more positions with one or more of $R_2$, $R_3$, $R_4$, and $R_5$, each of which may be the same or different.

2. The compound of claim 1, wherein W is O.

3. The compound of claim 1, wherein X is O, NH or S.

4. The compound of claim 1, wherein $R_1$ is H.

5. The compound of claim 1, wherein $R_2$, $R_3$, $R_4$, and $R_5$ are each H.

6. The compound of claim 1, wherein $R_6$ is phenyl or benzo[d][1,3]dioxolyl, each of which may be optionally substituted with one or more substituents independently selected from the group consisting of hydroxy, methoxy, methyl, $N(CH_3)_2$, $NH_2$, $-NHCOCH_3$, fluorine, bromine, and chlorine.

7. A pharmaceutically acceptable composition comprising a therapeutically effective amount of the compound of claim 1 and a pharmaceutically acceptable carrier.

8. A compound having the formula I:

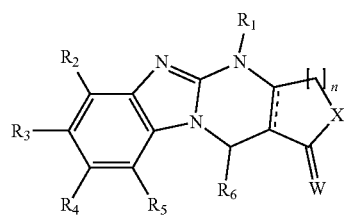

or a pharmaceutically acceptable salt, ester stereoisomer, or solvate thereof, wherein:

n is 1;

W is O;

X is O, NH or S;

$R_1$ is H;

$R_2$, $R_3$, $R_4$ and $R_5$ are each H; and $R_6$ is phenyl or benzo[d][1,3]dioxolyl, each of which may be optionally substituted with one or more substituents independently selected from the group consisting of hydroxy, methoxy, methyl, $N(CH_3)_2$, $NH_2$, $-NHCOCH_3$, fluorine, bromine, and chlorine.

9. A pharmaceutically acceptable composition comprising a therapeutically effective amount of the compound of claim 8 and a pharmaceutically acceptable carrier.

10. A compound selected from the group consisting of:
1
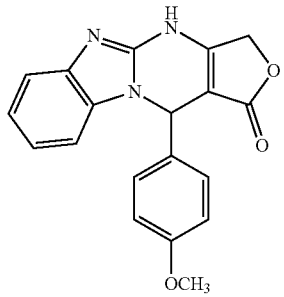
2
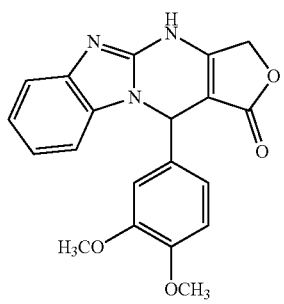
3
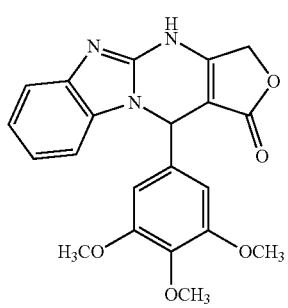
4
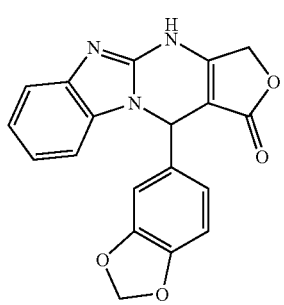
5
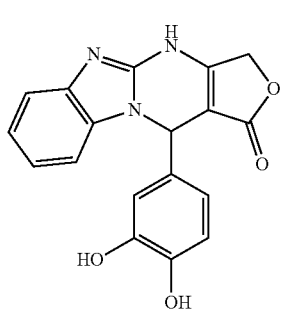
-continued
6
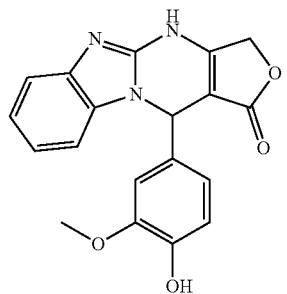
7
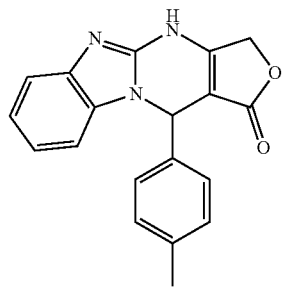
8
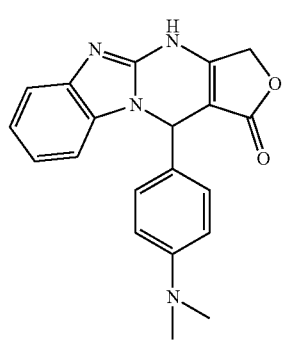
9
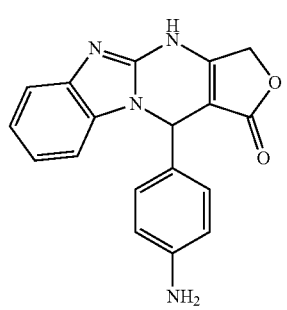
10
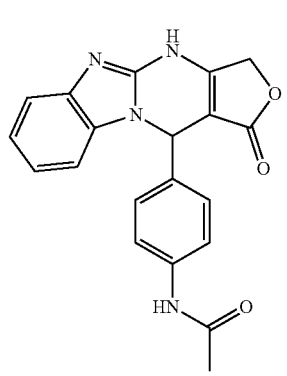

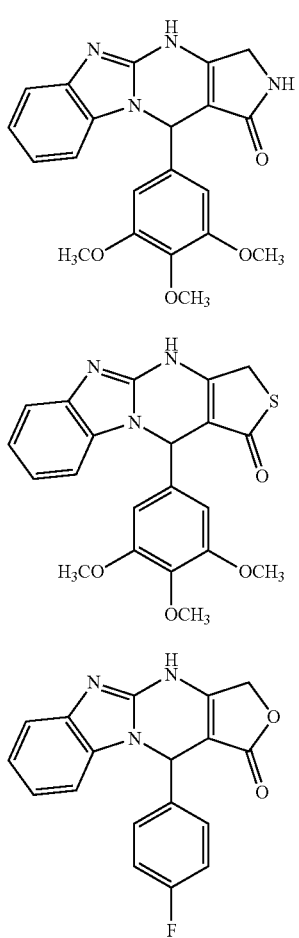
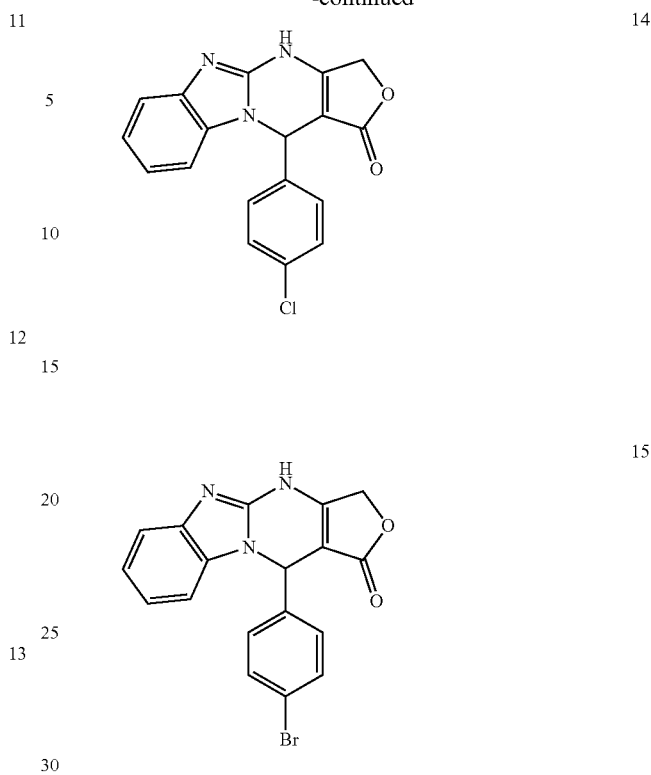
and a pharmaceutically acceptable salt, ester, stereoisomer, or solvate thereof.
11. A pharmaceutically acceptable composition comprising a therapeutically effective amount of the compound of claim 10 and a pharmaceutically acceptable carrier.
* * * * *